United States Patent
Becker et al.

(10) Patent No.: US 8,790,116 B2
(45) Date of Patent: Jul. 29, 2014

(54) ENDODONTIC FILE

(75) Inventors: Arik Becker, Doar-Na Emek HaYarden (IL); Haim Levy, Pardes Hana (IL); Shlomo Berkovich, Herzeliya (IL); Uri Katan, Kfar Sava (IL)

(73) Assignee: Medic NRG Ltd., Kibbutz Afikim (IL)

( * ) Notice: Subject to any disclaimer, the term of this patent is extended or adjusted under 35 U.S.C. 154(b) by 0 days.

(21) Appl. No.: 14/112,133

(22) PCT Filed: Apr. 1, 2012

(86) PCT No.: PCT/IL2012/000139
§ 371 (c)(1),
(2), (4) Date: Oct. 16, 2013

(87) PCT Pub. No.: WO2012/143918
PCT Pub. Date: Oct. 26, 2012

(65) Prior Publication Data
US 2014/0045142 A1 Feb. 13, 2014

(30) Foreign Application Priority Data

Apr. 17, 2011 (IL) .......................................... 212422
May 22, 2011 (IL) .......................................... 213042

(51) Int. Cl.
*A61C 5/00* (2006.01)
*A61C 5/02* (2006.01)

(52) U.S. Cl.
CPC ....................................... *A61C 5/023* (2013.01)
USPC ........................................ 433/102; 433/224

(58) Field of Classification Search
USPC .......................................... 433/102, 81, 224
See application file for complete search history.

(56) References Cited

U.S. PATENT DOCUMENTS

2005/0026109 A1   2/2005  Buchanan
2007/0099149 A1   5/2007  Levy et al.

FOREIGN PATENT DOCUMENTS

| EP | 1779804 A2 | 5/2007 |
| WO | 2008102321 A2 | 8/2008 |
| WO | 2008102352 A1 | 8/2008 |
| WO | 2011104705 A1 | 9/2011 |

OTHER PUBLICATIONS

International Search Report and Written Opinion for International Application No. PCT/IL2012/000139 dated Sep. 6, 2012.
International Preliminary Report on Patentability for International Application No. PCT/IL2012/000139 dated Jul. 5, 2013.

*Primary Examiner* — Ralph Lewis
(74) *Attorney, Agent, or Firm* — Dinsmore & Shohl LLP (57) ABSTRACT

An endodontic file for a motorized rotary handpiece includes a coupler element for coupling to the handpiece, a central longitudinal flexible core including a central flexible cable supported by the coupler element, and a helical wire surrounding the core and extending toward a tip of the core opposite the handle end. The flexible core includes a first plurality of inner strands twisted together in a first direction and surrounded by a second plurality of outer strands twisted in an opposite direction. The tip of the core is chamfered and unbonded and protrudes beyond the helical wire at the tip whereby in use reversing a direction of rotation of the endodontic file after the tip of the core reaches the apex of the root canal, unwinds the outer strands, which operate as a brush during removal of the endodontic file from the root canal.

29 Claims, 6 Drawing Sheets

ENDODONTIC FILE

CROSS REFERENCE TO RELATED APPLICATIONS

This application is a national-phase entry of International Patent Application No. PCT/IL2012/000139, filed Apr. 1, 2012 which International Application designates the United States and claims the benefit of priority to Israel Application No. 212422, filed Apr. 17, 2011 and Israel Application No. 213042, filed May 22, 2011.

FIELD OF THE INVENTION

The present invention relates to endodontic devices.

BACKGROUND OF THE INVENTION

Modern endodontic treatment involves removal of the damaged pulp, followed by cleaning and shaping of the root canal space, irrigating, and filling with biocompatible material such as gutta-percha and a root canal sealer.

Shaping of the canal is performed either manually, using a series of stainless steel hand-held files, or mechanically, using rotary nickel-titanium files adapted to fit a standard or dedicated dental handpiece.

The manual process relies on the experience of the dentist, is physically difficult to perform and is time-consuming. The use of files requires repeated changing between numerous different rat-tail files, progressively increasing from the smallest to the largest. Its reach to the apical constriction for widening and removal of the smear layer is limited. The reason for such limitations relates to the moderate elasticity of the steel files and the risk of fracture when excessive force is applied.

Although the field of elastic rotary nickel-titanium endodontic files has developed greatly over the last few years, fracture (separation) of nickel-titanium rotary files is still often reported, and hence the use of such is restricted. In order to overcome the fracture problem, a large range of dedicated handpiece systems, powered by slow speed transaction equipped with torque and speed control limitation circuits, have been developed, requiring a high level of professional skill for their operation. As a result, the cost of files and the related equipment per endodontic treatment has increased and instruments are typically operated only by experts in the endodontic field, while non-specialists use standard handpieces in a risky procedure.

Additionally the round cross-section of the file prevents adequate cleaning when the canal cross-section is oval or narrow in shape. In such cases, enlargement of the canal cross-section to accept the round cross-section of the file, may weaken or perforate the wall or the apical portion of the canal. The same risk of perforation applies in case of a curved root canal, where the file tends to follow the path of least resistance, acting rigorously on the convex walls within the reach of the file, and insufficiently over the concave portions.

US20070099149 entitled "Endodontic device and method of utilizing and manufacturing same" corresponding to IL 171705 in the name of the present applicant discloses an endodontic device for cleaning, filing or reaming root canals. The device includes one or more metallic, flexible strands having an edge, a working section, a connecting section and a coupling head connected thereto. The strands are coated along the working section with a thin layer of a binder having abrasive particles embedded therein. The flexible, longitudinal strands are so constructed that their outer surfaces serve as active filing surfaces.

In operation the strand section of the endodontic file is inserted into the root canal to the apex, and the strand or strands are mechanically rotated by a handpiece to a high speed. The thin, flexible portion of the device is centrifugally thrown against the canal wall following the natural curvature and complex cross-section of the root canal in exact manner. The whole contents of US20070099149 are incorporated herein by reference.

WO2008/102321 entitled "Endodontic file" corresponding to IL 181439 in the name of the present applicant and likewise incorporated herein by reference, teaches an endodontic file comprising at least one cord and a wire wound around at least a major portion of the cord, the wire having an abrasive outer surface.

WO/2011/104705 entitled "Rotary Endodontic File with Frictional Grip" corresponding to IL 204195 filed in the name of the present applicant and likewise incorporated herein by reference, teaches an endodontic file similar to that described in WO2008/102321 but having an elastomeric grip partially covering the helically wound wire near a first end thereof and having an outer diameter that is slightly wider than an internal diameter of a barrel of a dental instrument whereby on insertion into the barrel it is supported therein only by friction.

Conventional endodontic reamers are hand-held but the reamers described in the above-referenced publications are configured for rotation at low speed by an electrical motor. By "low-speed" is meant less than 40,000 rpm as distinct from the "high-speed" of 300,000-40,000 rpm at which dental drills are rotated. It will be appreciated that the terms "low" and "high" in this context are relative since a rotation speed of 30,000 rpm is certainly "high" compared to conventional manual reamers. To this end, the reamers in all of the above-referenced publications include a central cord around a major portion of which there is wound a wire having an abrasive outer surface. In practice, the central cord comprises not a single low gauge (i.e. high diameter) wire but rather a plurality of high gauge (i.e. low diameter) wires that are twisted together to afford high flexibility, which is obviously important in root canal treatment. In order to prevent the wires from untwisting during treatment, the tips of the wires are welded to form a hemi-spherical bulb that takes no part in the root canal procedure other than to prevent the free ends of the wires from untwisting. The hemi-spherical bulb also ensures that tip of the file does not damage the inner wall of the root canal on contact therewith and helps to reduce the likelihood of the file sticking against an inner surface of the root canal, even though this cannot be entirely prevented.

In order to accommodate undesirable sticking, which could result in breakage of the endodontic file, WO/2011/104705 limits the transmitted torque by employing a friction grip that allows the tool to slip within its coupler.

Current solutions for rotary preparation are based on different types of Nickel-Titanium files. The level of skill required by the dentist is high, and the supplies are expensive thus ruling out use of such files for all but a small fraction of practitioners. Moreover, notwithstanding the improvements to endodontic files contemplated by the above-referenced prior art, shaping of the root canal still requires use of multiple files, resulting in root canal treatment being tedious for the dentist and uncomfortable for the patient.

It would therefore be desirable to simplify root canal preparation while avoiding the weaknesses of existing products leading to file breakage, perforations, ledging, and penetration of the periapical tissue. It is also desirable to reduce the treatment time, compared to current endodontic files and procedures.

SUMMARY OF THE INVENTION

In accordance with one aspect of the invention there is provided an endodontic file for a motorized rotary handpiece, said endodontic file comprising:
- a coupler element for coupling to the handpiece,
- a central longitudinal flexible core including a central flexible cable supported at a handpiece end by said coupler element, and
- a helical wire at least partially surrounding the core and extending toward a tip of the core opposite the handle end;
- the tip of the core being chamfered and unbonded and protruding beyond the helical wire at the tip.

The invention enables most dentists to use only one or two files to complete canal preparation within 1 or 2 minutes.

In one embodiment, the cord is of a diameter between 0.15 mm to 0.3 mm and includes a central flexible cable comprising a first plurality of twisted wires that are surrounded by a second plurality of twisted wires twisted in an opposite direction to the first plurality of twisted wires. In use, the file is used to penetrate and expand the root canal while rotating the file in a direction that tends to tighten both the helical wire and second plurality of twisted wires. During this procedure the dentist applies downward pressure on the file that forces the file forward and cuts through the root canal forming debris and filings. When the file has reached the apical constriction, it is then withdrawn also at high speed but in an opposite direction. This unwinds the second plurality of twisted wires, which are of very low diameter and open to form a brush that sweeps away the debris and filings on its way out of the root canal.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the following description of some embodiments, identical components that appear in more than one figure or that share similar functionality will be referenced by identical reference symbols.

Figures 3A, 3B, 3C:
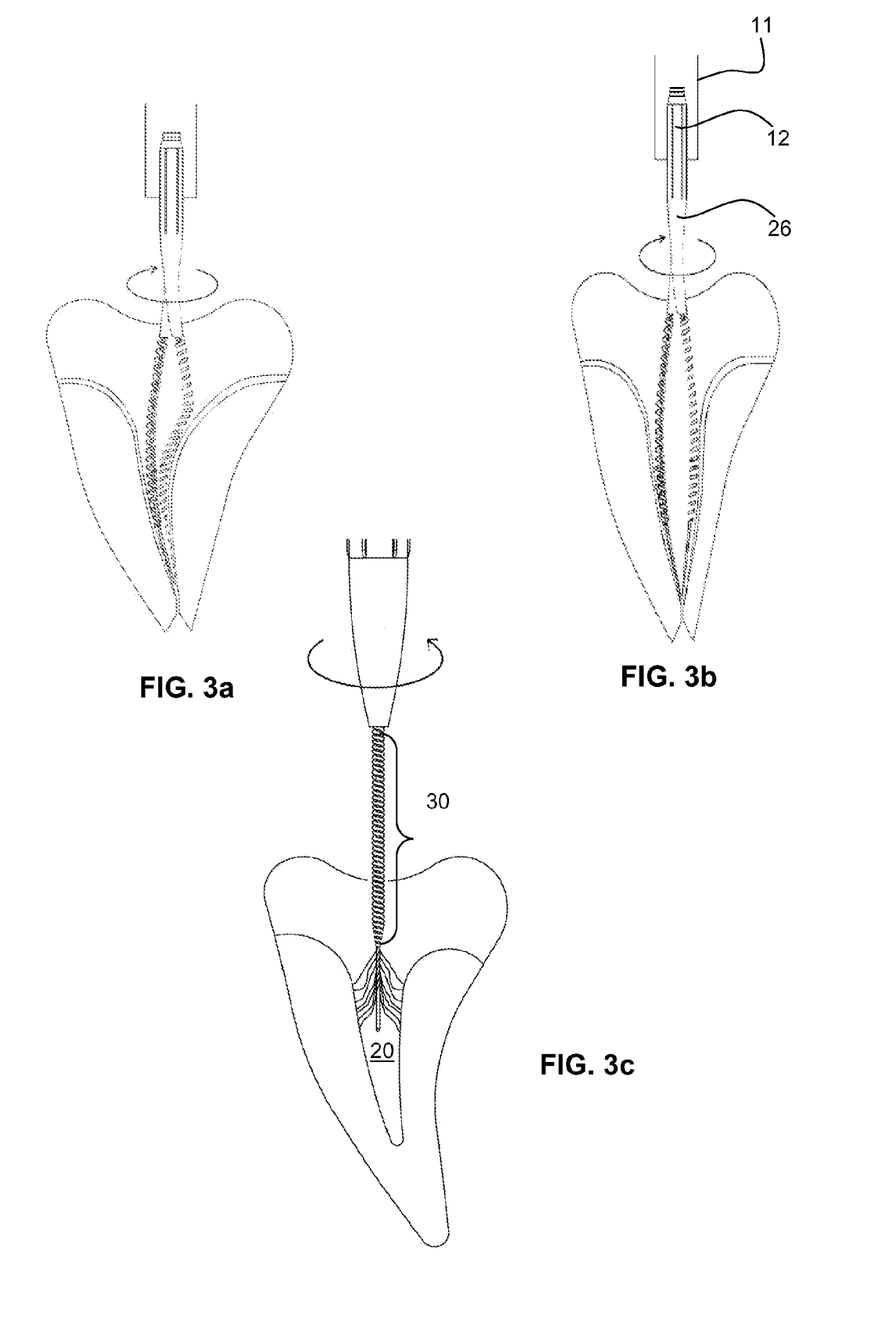
FIGS. 3a and 3b show views of the endodontic file of FIG. 1 during and after use.
FIG. 3c shows pictorially reverse rotation during removal of the endodontic file of FIG. 1 after preparation of the root canal so as to operate the file in "brush" mode.

Referring to the figures there is shown an endodontic file 10 to be utilized with a rotary handpiece 11 capable of rotating at speeds of 6,000 to 40,000 rpm. The file 10 permits complete canal preparation in a single, time-saving procedure after the first canal opening is made, typically using the smallest applicable hand-held file thickness, which is normally of diameter 0.10 mm to 0.15 mm. As best seen in FIG. 3a, the file 10 comprises a coupler element 12 for coupling to the handpiece 11 and a central longitudinal core 13 anchored at a first end 14 (see FIG. 6a) within the coupler element. Thus, in use, the first end 14 is secured within the handpiece and, to this end, will be referred to throughout the following description and claims as the "handpiece end." A helically wound wire 15 at least partially surrounds the core 13 and is wound clockwise so that when the file is rotated in a clockwise direction, the helical wire 15 tends to tighten. This prevents the helical wire 15 from opening upon insertion of the file into the root canal, thus avoiding it snagging the internal wall thereof. The helical wire 15 extends toward a second end 16 of the cord opposite the handle end 14, which protrudes beyond the helical wire and will be referred to throughout the following description and claims as the "tip". The file is characterized in that unlike known endodontic files, the tip 16 of the core is chamfered and unbonded. The reasons for this and the surprising benefits that result therefrom will become apparent from the following description.

Figure 1A:
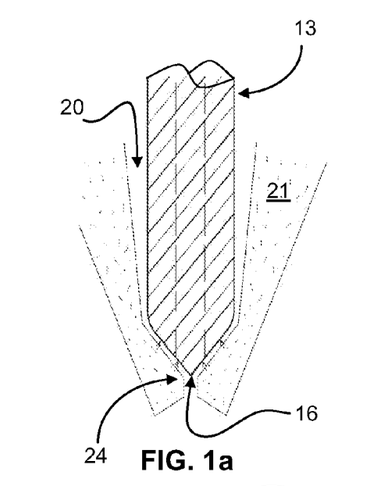
FIGS. 1a, 1b and 1c are pictorial views showing the tip of an endodontic file according to different embodiments of the present invention.
Figure 1B:
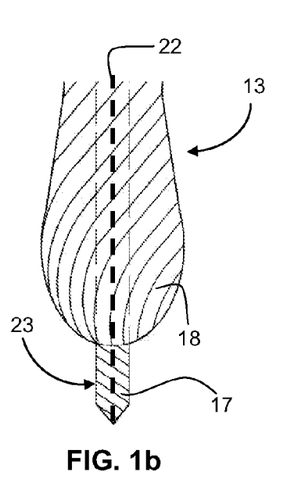
Figure 1C:
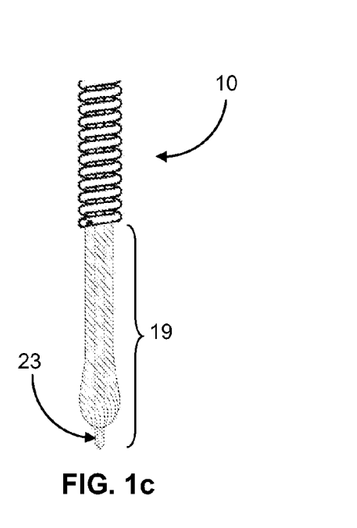
Figure 2A:
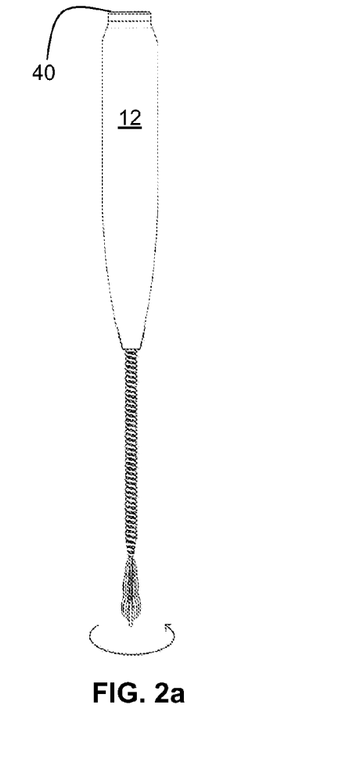
FIGS. 2a and 2b show views of the endodontic file of FIG. 1 in brush mode.
Figure 2B:
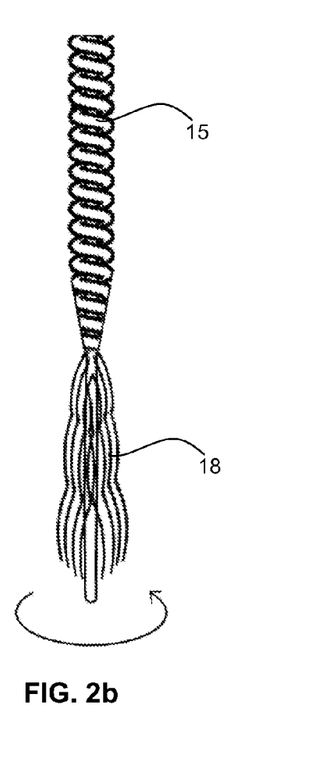

Referring to FIG. 1a, there is shown schematically a root canal 20 having an inner wall constituted by a dentin layer 21, which is worked by the endodontic file 10. The core 13 typically comprises a central single cord 22 shown in dotted outline in FIG. 1b, around which a small number of inner strands 17 (constituting a first plurality and typically 4-10) are wound in a first direction to form a central flexible cable, and a second plurality of outer strands 18 (typically 8-15) are wound in an opposite direction around the central flexible cable. FIG. 1a shows an initial configuration where the inner strands 17, shown in dotted outline, do not yet protrude forward of the outer strands 18. It is thus seen that initially at the tip 16 the inner and outer strands form a unitary structure, which is filed to remove material at the tip 16 thus forming a sharp point. However, when the file 10 is inserted in the narrow root canal 20 and the outer strands 18 meet resistance, owing to the tapering of the root canal, the outer strands 18 are obstructed by the internal wall of the root canal are pushed back thereby causing them to retreat and allowing the core 13 to protrude and facilitate penetration into the apical constriction 24. In so doing, the outer strands 18 form a substantially spherical bulb as shown in FIGS. 1b and 1c through which the tip of the core penetrates. This effect is realized only by virtue of the tip 16 of the file not being bonded. The spherical shape shown in FIGS. 1b and 1c results from the packing of the outer strands 18 into a confined space, whereby the strands pile up on top of each other and bunch into a substantially spherical bulb. In one embodiment, the second plurality of outer strands 18 are wound in the same sense as the helical wire 15, so as to be tightened when the file is rotated clockwise upon insertion of the file into the root canal. The diameter of the core is typically 0.15-0.30 mm and is half the diameter of the combined inner and outer strands. When the core protrudes, it enables the file to reach the last millimeter of the root canal, to the apical constriction, even in a very narrow canal. However, penetration of the tip into the apical constriction is not a requirement since in narrow root canals the outer strands may well be pushed back before the tip reaches the apical constriction and, in doing so, the strands exert lateral pressure on the narrow inner wall of the root canal thereby widening it more effectively than hitherto-proposed constructions.

This is not possible in known devices where the tip of the core comprises multiple strands that are welded or otherwise treated to form a rounded tip or where the core includes a cable that is treated to form a rounded tip, since in both cases the resulting large diameter militates against the tip of the core reaching the apical constriction. The inner and outer strands of the core 13 are stainless steel fibers of circular cross-section having a diameter in the order of 0.03-0.06 mm. They are not roughened or otherwise abraded but form a natural rough surface owing to the peaks and troughs caused by the juxtaposition of multiple narrow fibers.

The central longitudinal core 13 may be made of twisted thin stainless-steel strands. A typical core 13 is between 0.15 mm to 0.3 mm in diameter, the inner strands 17 having a diameter that is approximately half that of the core, i.e. 0.10 mm to 0.15 mm. The core 13 is firmly secured at a second end thereof to the helically wound wire 15. This may be done by tight coiling of several turns of the helically wound wire 15 around the core 13. The core 13 can be secured to the helically wound wire 15 at the handle end by soldering, brazing, welding or gluing. The core 13 is longer than the surrounding helically wound wire 15, leaving an exposed portion 19 (shown in FIGS. 1*c* and 6*a*) of 2 to 9 mm near the tip 16 which is chamfered to a depth of approximately 0.5 mm by a grinding, polishing or etching process.

Figures 6A, 6B:
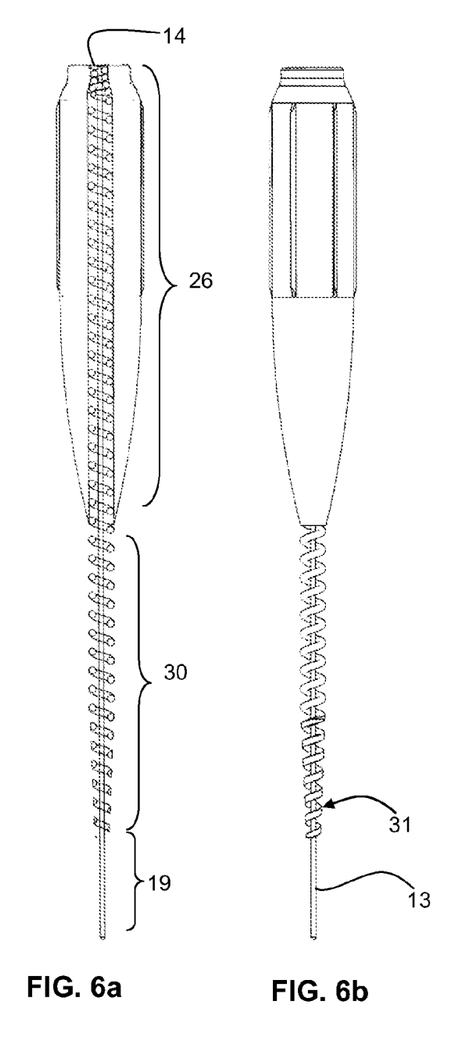
FIGS. 6a and 6b are pictorial representations of a dedicated brush file according to an embodiment of the invention.

The surrounding helically wound wire 15 may be made of stainless-steel having a diameter of 0.2 to 0.4 mm. As best seen in FIGS. 3*a* and 6*a*, the helically wound wire 15 is divided along its length into two portions, an inactive portion 26 mostly covered by the coupler element 12 and an active portion 30 typically between 8 mm to 15 mm in length and at least partially roughened to form an abrasive layer. As shown in FIGS. 6*a* and 6*b*, the pitch of the helically wound wire 15 may vary so as to be higher (i.e. more spaced apart) in the active portion 30 than toward the tip such that remote from the tip adjacent coils are more spaced apart, providing additional free space for debris capture. This also has the effect of rendering the file more flexible toward the tip owing to the closer spacing of the windings. Optionally different portions of the helically wound wire 15 may be wound with varying pitch. It will be noted however, that only a few turns at the handle end are tightly coiled over the core 13, the majority by length of the helically wound wire 15 being loosely wounded over the core 13 including the tapered portion 16 (FIG. 1*b*), such that a very small annular gap of between 0.01 mm to 0.2 mm exists between the core 13 and the helically wound wire 15 along at least the entire length of the active portion 30. The free radial play of the core 13 in the helically wound wire 15 helps to prevent high strain on the core 13 when inserted into a curved canal and to independent operation of the core when the helically wound wire 15 is restricted in motion. As also seen in FIGS. 6*a* and 6*b*, the helical winding 15 is tapered toward the tip by grinding to form a thinner tail 31 close in diameter to that of the core. This, too, has the effect of rendering the file more flexible toward the tip.

In one embodiment, the coupler element is made of an elastomer grip formed of rubber or thermoplastic elastomer, preferably injection or pressure molded directly over the core 13 and helically wound wire 15. Optionally the elastomer grip can be elastically stretched, bonded or heat shrunk over the helically wound wire 15. The grip is advantageously cylindrical 32 with a conical extension 34 tapering to a very thin cover 36 towards the active portion 30 of the helically wound wire 15. The conical extension 34 of the grip 16 constitutes a transitional flexibility zone between the gripping cylinder 32 and the active portion 30 of the helically wound wire 15. Specific hardness properties of the grip material are selected to provide effective stress relieving of the helically wound wire along the conical extension 34 of the grip during operation. The cylindrical portion 32 of the grip is frictionally inserted into the mounting barrel of a standard or dedicated handpiece for imparting rotational movement to the file, no other locking means is used. It will be understood that the imparted torque is limited by the percentage of squeeze of the cylinder 32 during insertion to the mounting barrel and by the coefficient of friction between the elastomeric material of the grip and the metal barrel of the handpiece. Accordingly the maximal transmitted torque can be calculated or otherwise experimentally observed for any specific combination of external diameter of the cylinder 32 and elastomeric raw material. Furthermore, the desired maximal transmitted torque can be precisely controlled and constantly repeated in a mass production of files 10 made in accordance with the present invention.

The grip is optionally provided with a short top section 40 of reduced diameter, on which a metal cap (not shown) can be conductively attached to the central core 13 using a conductive binder such as solder, laser weld or metal filled epoxy. The metal cap may serve as an electrical reference point for an apex locator, as known per se. In such an embodiment, transfer of torque from the handpiece to the file 10 is based only on friction. The effect of this method turns the file grip into a sort of safety coupling. This guarantees that when the shear force between the file 10 and the root canal increases, for any reason, beyond a certain value, the grip will slip in the handpiece barrel. This avoids breakage damage to the file as well as any undesirable damage to the dentin layer. The standard locking latch mechanism of the handpiece is eliminated.

With reference to FIGS. 3*a* to 3*c*, the method of usage of the file 10 is described. In operation, the file 10 is attached to a standard or dedicated handpiece as described above and inserted into the root canal 20 (FIG. 5) of a tooth 50. Manual back and forth motion is provided while the handpiece is set to rotate at speed of between 6,000 to 30,000 rpm and irrigation is supplied. The slender, working section of the file 10 is centrifugally thrown against the internal dentin layer 21 of the canal wall following the natural curvature and complex cross-section of the root canal in exact manner. The abrasive layer gently buffs and polishes the dentin layer 21, leaving a smooth and clean surface with no smear traces. Back and forth motion enables introduction of lubricant and rinse of debris with a constant stream of water irrigation supplied by the handpiece as known per se.

When enlarging the root canal, the direction of rotation of the file as shown by arrows in FIGS. 3*a* and 3*b* is in the sense that will further tighten the twist of the outer strands 18 of the core 13 and of the helically wound wire 15. Once the tip of the core reaches the apical constriction 24, the file is rotated in the opposite direction as shown in FIG. 3*c* while simultaneously withdrawing the file from the root canal. This has the effect of unwinding the twisted outer strands 18 of the core thereby forming a brush as shown in FIG. 3c providing highly effective removal of debris that are formed by the helical wire during insertion of the file. Such a procedure allows the root canal to be cut and finished from the root up when moving from the apical third towards the crown third, which is the opposite to conventional procedures that working from the crown down to the apical constriction.

Figure 4A:
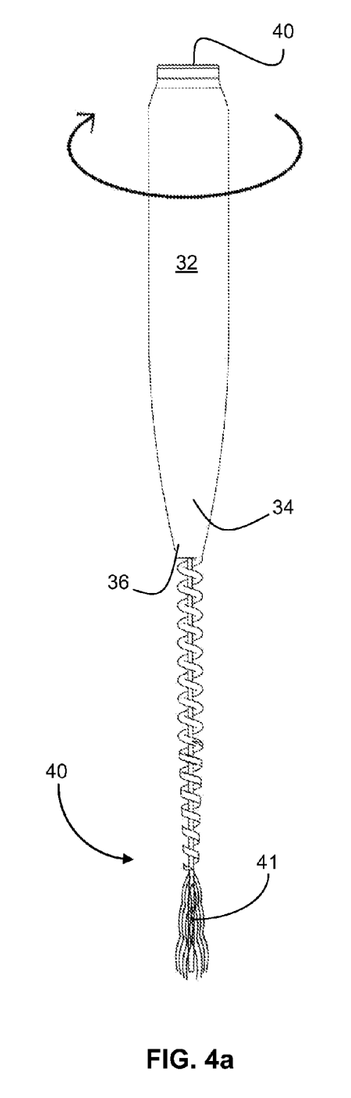
FIGS. 4a and 4b are pictorial representations of a dedicated brush file according to an embodiment of the invention.
Figure 4B:
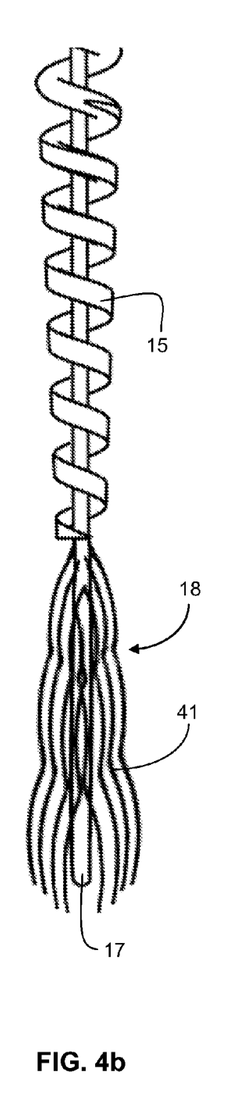
Figure 5A:
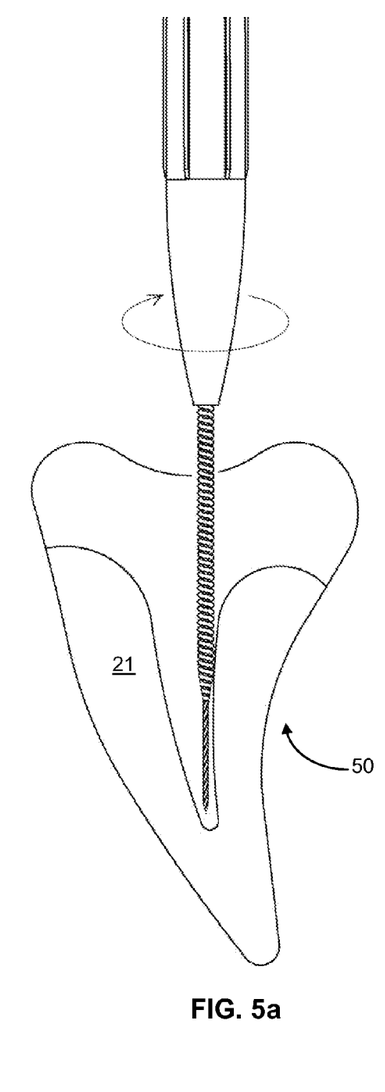
FIGS. 5a and 5b are pictorial representations showing different modes of operation of the file in a root canal of a tooth.
Figure 5B:
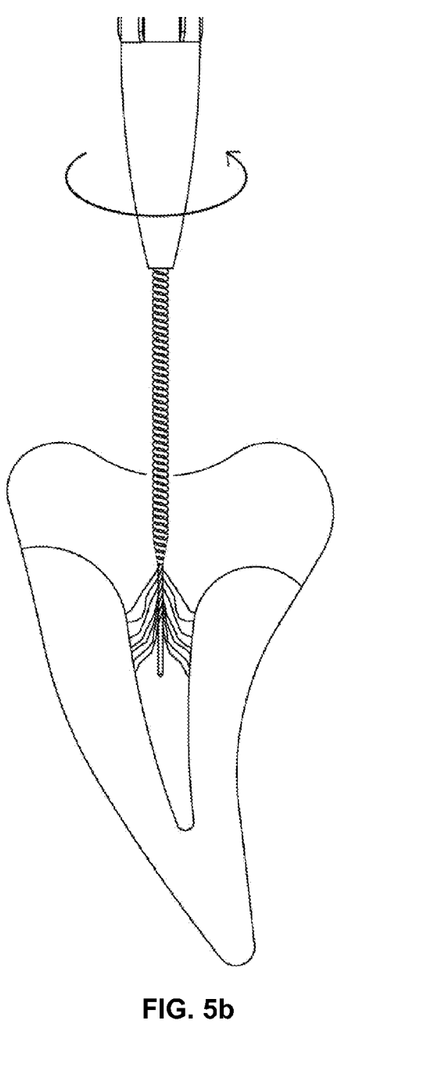

FIGS. 4a and 4b show a dedicated brush file 40 according to another embodiment, where the core 13 is not configured to allow retraction of the outer strands 18, but where the outer strands are nevertheless configured to unwind upon withdrawal of the file so as to form a brush 41. In such an embodiment, the outer strands 18 of the core are wound in the opposite sense of the helical winding 15. In use, the root canal cavity is prepared in any suitable manner, such as described above with reference to FIGS. 3a and 3b. Once the root canal cavity is finished, liquid irrigation is applied and the brush file 40 is inserted without rotation or at very low speed i.e. about 100-200 rpm of the handpiece to which it is attached. When the file is fully inserted into the root canal, the handpiece is rotated clockwise at full speed while at the same time withdrawing the file. This induces the helical winding 15 to tighten since it is wound clockwise, while unwinding the second strands 18, owing to their being wound anti-clockwise, which consequently open to form a brush 41, which sweeps away remaining debris produced during root canal preparation by the irrigation liquid as well as fine surface deposits that are removed by the brush. In this case, since the root canal is already prepared, there is not a continuously generated accumulation of debris that requires removal and so a constant stream of irrigation liquid is not required. It will be appreciated that the same effect could be realized by winding the helical winding 15 anti-clockwise and the second strands 18 clockwise, and rotating the handpiece anti-clockwise when withdrawing the file.

Thus, the outer strands 18 serve two functions. In the first embodiment, they retract upon contact with the narrow inner surface of the root canal so as to expose the inner strands, which can thereby reach to the apical constriction, while opening to form a brush when the file is rotated in an opposite direction during withdrawal. In this mode of operation, the resulting widening of the outer surface of the core near the apical constriction also increases the abrasive effectiveness of the file and helps to widen the root canal. In the second embodiment relating to a dedicated brush file, the outer strands 18 do not participate in widening the root canal but serve only to open and form a brush when the file is rotated during withdrawal.

Figure 7A:
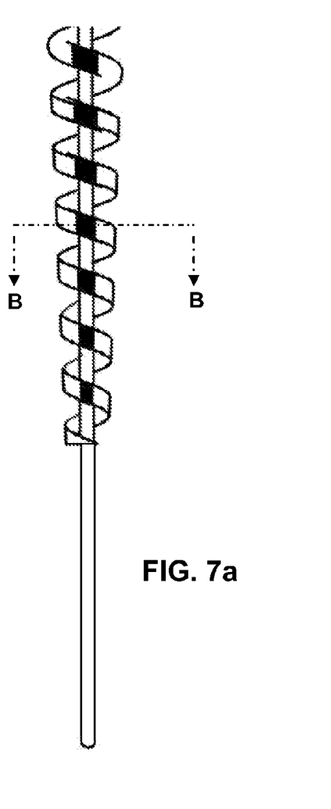
FIG. 7a is a pictorial representation showing a detail of the helical winding in an embodiment of the invention.
Figure 7B:
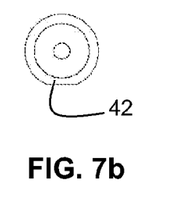
FIGS. 7b and 7c show elevations through the line B-B in FIG. 7a according to different embodiments.

FIG. 7a shows an embodiment of either the file or dedicated brush, where an outer surface of the helical winding 15 is ground to form a flat surface 42 as shown in elevation in FIG. 7b whereby the helical winding has a D-shaped cross-section. When such a file is rotated in the root canal, the sharp corners of the D-shaped cross-section cut into the dentin thereby enhancing the cutting efficiency of the file.

The flat surface of the D-shaped profile may be continuous or each loop of the helical wire 15 may be flattened independently after winding the wire so as to form multiple D-sections whose sharp corners are mutually angularly offset, so that looking down the helical wire there are multiple sharp corners that are mutually offset like steps in a spiral staircase. The cutting effect is thereby enhanced since upon inserting the file into the root canal, a progression of corners each emanating from a different edge of the helical wire cuts through the root canal.

Figure 7C:
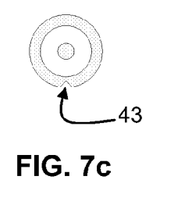

FIG. 7c shows an alternative configuration where, instead of, or in addition to, the D-shaped sections, one or more longitudinal slots 43 are cut into the helical wire, thereby creating sharp edges which have a similar effect.

Although the core of the file is preferably formed from a single central cable, it will be understood that this is not essential and the central cable may have more than one wire. Likewise, while the core is preferably formed of two layers of strands wound in mutually opposing directions, it is to be understood that this is not intended to be limiting since the essential novelty of the core resides in its ability to reach into the apical constriction by virtue of its tip being chamfered and unbound. Likewise, while the ability of the outer strands to unwind is an important benefit of the invention, it is not considered essential that the outer strands be wound on a layer of inner strands in mutually opposite senses. The inventors have found that the use of an inner layer improves adhesion of the outer strands owing to their being wound in mutually opposite senses, but one skilled in the art will doubtless conceive of alternative approaches to improving the adhesion of the outer strands without necessitating an inner layer.

Figures 8A, 8B, 8C:
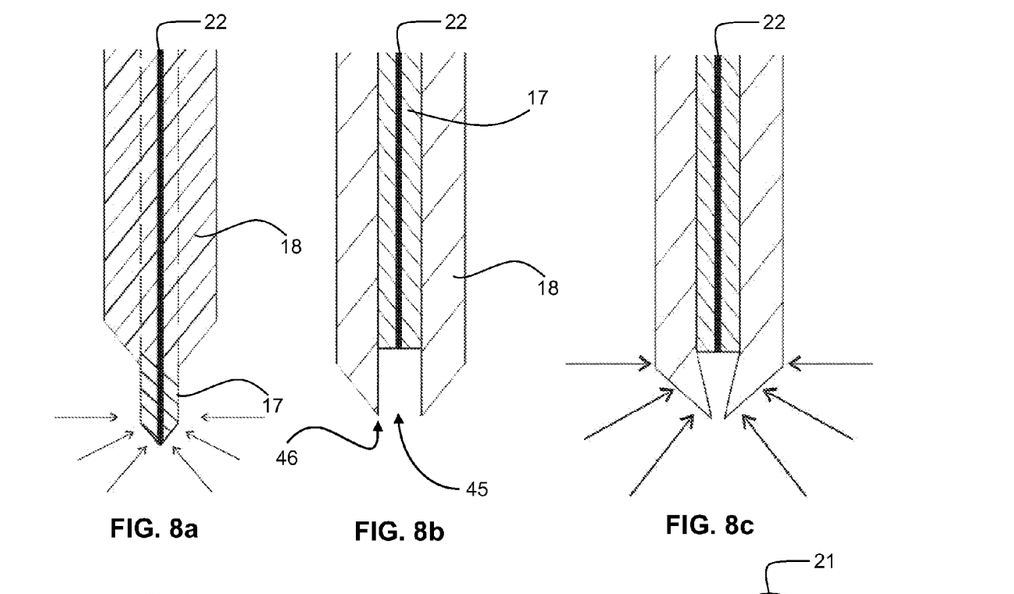
FIGS. 8a to 8c are schematic representations showing a detail of the tip of the file according to different embodiments of the invention.

In the embodiments as described, the inner strands and the outer strands form a composite tip and meet at a common outer surface of the core. However, as shown in FIG. 8a, the invention also embraces the possibility that also before use the inner strands protrude slightly as shown in FIG. 1c. Thus, it is seen that the inner strands 17 protrude beyond the outer strands 18 thus facilitating penetration into the end of the root canal.

FIGS. 8b and 8c show an alternative configuration where the inner strands 17 are initially hidden within the outer strands 18 so as to form a slight hollow 45 at the end of the core having an inner wall 46. In this case, contact between the outer strands (18) and the inner wall of the root canal exerts lateral pressure on the outer strands (18) thereby causing the inner wall 46 to collapse inward and narrow the tip.

Figure 9A:
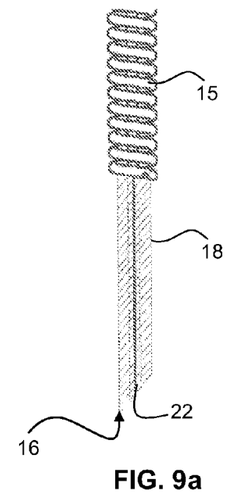
FIGS. 9a and 9b are pictorial representations showing a modification to the tip of the endodontic file according to a different embodiment of the invention.

In the embodiments so far described, the tip 16 of the core 13 is chamfered circumferentially to form an apex that is symmetrically disposed relative to the core such that the outer strands 18 are exposed symmetrically around the complete periphery of the core 13. However, it is to be noted that beneficial results are obtained even when the tip 16 is chamfered asymmetrically even to the extent that the outer strands 18 are not exposed around the complete periphery of the file as shown in FIGS. 1a and 1b, for example, but are exposed around only part of the periphery such as shown in FIGS. 9a and 9b.

In the embodiments so far described with reference to FIG. 1a, the core 13 is a multi-strand flexible cable comprising a central single cord 22, around which a first plurality of inner strands 17 are wound in a first direction, and a second plurality of outer strands 18 are wound in an opposite direction. However, beneficial results are obtained even when the central core 13 is formed of a single unitary cable or wire. In one embodiment reduced to practice, a Nickel-Titanium wire of diameter 0.15-0.30 mm was employed. Apart from this distinction, the core 13 appears to the naked eye to look much the same as the multi-strand core shown in FIG. 6a, which shows that the core 13 is longer than the surrounding helically wound wire 15, leaving an exposed portion 19 of 2 to 9 mm near the tip 16 which is chamfered to a depth of approximately 0.5 mm by a grinding, polishing or etching process. The core is still sufficiently flexible to navigate through the root canal, whilst its increased rigidity relative to the multi-strand core allows a longer length of the core 13 to protrude from the end of the helical wire 15 than is possible with the multi-strand core.

Figures 9B, 10A, 10B, 10C:
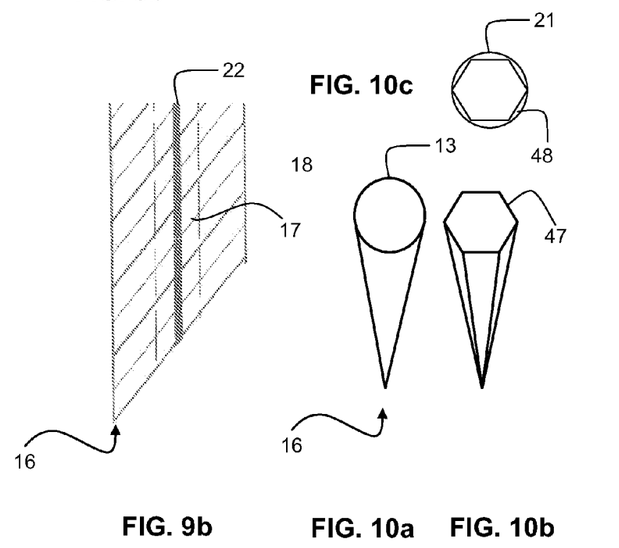
FIGS. 10a, 10b and 10c are pictorial representations showing details of an endodontic file according to yet a different embodiment of the invention.

FIG. 10a shows a first embodiment where the tip 16 of the wire is symmetrically chamfered to form a conical tip. FIG. 10b shows a second embodiment where the conical tip 16 is chamfered to form one or more flat surfaces 47. The flat surfaces 47 have sharp corners that cut into the dentin thereby enhancing the cutting efficiency of the file.

FIG. 10c is a plan view showing schematically the tip 16 shown in FIG. 10b cutting through the inner wall constituted by the dentin layer 21 of the root canal. It is seen that the flat surfaces 47 create respective hollow passages 48 abutting the root canal wall, which serve as channels for conveying lubricant or water irrigation.

It will be evident to those skilled in the art that the invention is not limited to the details of the foregoing illustrated embodiments, the scope of the invention being indicated by the appended claims.

The invention claimed is:

1. An endodontic file for a motorized rotary handpiece, said endodontic file comprising:
   a coupler element for coupling to the handpiece,
   a central longitudinal flexible core including a central flexible cable supported at a handpiece end by said coupler element, and
   a helical wire at least partially surrounding the core and extending toward a tip of the core opposite the handle end;
   the tip of the core being chamfered and unbonded and protruding beyond the helical wire at the tip;
   wherein:
   the core includes a plurality of outer strands surrounding the inner central flexible cable and being wound in a winding direction so that during use when the file is rotated in a direction opposite to said winding direction while at the same time withdrawing the file from a root canal, the outer strands unwind and open to form a brush.

2. The file according to claim 1, wherein the outer strands are wound in an opposite sense to the helical wire so that rotating the file in the winding direction of the helical wire both tightens the helical wire and unwinds the outer strands.

3. The file according to claim 1, wherein the helical wire is wound with a variable pitch along its length, such that different portions of the helically wound wire are of different pitch.

4. The file according to claim 1, wherein the inner central flexible cable of said core includes a plurality of inner strands twisted together in a first direction around a central flexible wire.

5. The file according to claim 4, wherein the outer strands surround the inner strands and are twisted in an opposite direction to the inner strands.

6. The file according to claim 1, wherein the outer strands are wound in an identical direction to that of the helical wire.

7. The file according to claim 1, wherein the central flexible wire and the plurality of strands are chamfered at the tip and are longer than the surrounding second plurality of twisted strands.

8. The file according to claim 1, wherein the central flexible wire protrudes beyond the plurality of inner strands at the tip.

9. The file according to claim 1, wherein the core is formed of a single unitary cable or wire having an end that is chamfered to form a substantially conical tip.

10. The file according to claim 9, wherein the conical tip is chamfered to form one or more flat surfaces.

11. The file according to claim 1, wherein the core is firmly secured at the handpiece end thereof to the helically wound wire by tightly coiling several turns of the helically wound wire around the core, followed by any one of soldering, brazing, welding and gluing.

12. The file according to claim 1, wherein the helically wound wire is divided along its length into an inactive portion accommodated within the coupler element and an active portion of between 8 to 15 mm in length, at least of the outer surface of the active portion being abraded to form an abrasive outer surface.

13. The file according to claim 12, having an intermittent spiral having an abrasive outer surface on alternate coils of the wire along at least part of the active portion.

14. The file according to claim 1, wherein the helically wound wire has a pitch that is larger than the wire diameter particularly in the active portion such that adjacent coils are spaced apart.

15. The file according to claim 1, wherein the helically wound wire is wound over the core in such a manner as to leave a slight annular gap between the helically wound wire and the core.

16. The file according to claim 1, wherein the coupler element comprises an elastomeric grip partially covering the helically wound wire near the handpiece end thereof and having an outer diameter that is slightly wider than an internal diameter of a barrel of the handpiece whereby on insertion into the barrel it is supported therein only by friction.

17. The file according to claim 16, wherein hardness properties of said elastomeric grip are selected to provide effective stress relieving of the helically wound wire along said conical extension of the elastomer grip during operation.

18. The file according to claim 1, wherein an outer surface of the helical wire is ground to form a flat surface whereby the helical wire has a D-shaped cross-section thereby enhancing cutting efficiency of the file.

19. The file according to claim 18, wherein the flat surface is continuous along a length of the helical wire.

20. The file according to claim 18, wherein the flat surface comprises a plurality of discrete flat surfaces that are mutually angularly offset along the helical winding.

21. The file according to claim 1, wherein an outer surface of the helical wire is provided with a longitudinal slot.

22. The file according to claim 1, wherein the tip is chamfered around at least a part of a periphery of the core such that the outer strands are at least partially exposed around the complete periphery of the file.

23. A method for finishing a prepared root canal of a tooth during endodontic treatment using an endodontic file according to claim 1, the method comprising:
   preparing the root canal using any suitable technique;
   attaching the endodontic file to a rotary handpiece;
   inserting the endodontic file into the prepared root canal without rotation of the handpiece or just slightly at very low speed; and
   when the endodontic file is fully inserted into the root canal, rotating the handpiece at full speed in a direction opposite to said winding direction while at the same time withdrawing the file so as to induce the helical winding to tighten while unwinding the second strands, which consequently open to form a brush, which sweeps away surface deposits.

24. The method according to claim 23, including applying liquid irrigation prior to insertion of the endodontic file into the root canal to assist in removal of the surface deposits.

25. A method for preparing a root canal using the endodontic file according to claim 1 attached to a rotary dental handpiece, the method comprising:
   opening the root canal using a hand-held file of minimal applicable thickness;
   inserting the coupler element of said file into the mounting barrel of a dental handpiece; and imparting rotational movement to the file at speed of between 51,000 to 40,000 rpm while applying axial pressure thereto so as to urge the file into the root canal toward the apex thereof, whereupon the helical wire is pushed by an inner wall of the root canal toward the handpiece end thus exposing the tip of the core and allowing it to reach the apex of the root canal.

26. The method according to claim 25, further including reversing a direction of rotation of the endodontic file after the tip of the core reaches the apex of the root canal, thereby unwinding the outer strands, which operate as a brush during removal of the endodontic file from the root canal.

27. The method according to claim 25, further comprising:

manually moving the handpiece back and forth so as to enable introduction of lubricant and rinse of debris with the constant water irrigation supplied by the handpiece.

28. The method according to claim 25 further including penetrating the apical constriction with the exposed tip.

29. A method for preparation of a root canal of a tooth during an endodontic treatment using an endodontic file according to claim 1, the method comprising:

opening the root canal using a hand-held file of minimal applicable thickness;

attaching the endodontic file to a handpiece;

inserting the working section of the file into the root canal;

setting the handpiece to rotate at speed of between 6000 to 40000 rpm;

providing irrigation;

using resultant centrifugal forces acting about the slender working section of the file, which is thrown against the internal dentine layer of the canal wall following the natural curvature and complex cross-section of the root canal in exact manner, thereby providing complete canal preparation in a single time-saving procedure; and using contact between the outer strands and the inner wall of the root canal to push back the outer strands thereby exposing the tip.

* * * * *